United States Patent [19]

Uchikubo et al.

[11] Patent Number: 4,891,695
[45] Date of Patent: Jan. 2, 1990

[54] ELECTRONIC ENDOSCOPE APPARATUS PROVIDED WITH A PLURALITY OF ENDOSCOPES HAVING SOLID STATE IMAGING DEVICES WITH AT LEAST ONE IDENTICAL PIXEL FORMING ELEMENT

[75] Inventors: Akinobu Uchikubo; Masao Uehara; Masahide Kanno, all of Hachioji; Jun Hasegawa, Hino; Masahiko Sasaki, Hachioji; Katsuyuki Saito, Hachioji; Katsuyoshi Sasagawa, Hachioji; Shinji Yamashita, Hachioji, all of Japan

[73] Assignee: Olympus Optical Co. Ltd., Tokyo, Japan

[21] Appl. No.: 292,144

[22] Filed: Dec. 30, 1988

[30] Foreign Application Priority Data

Feb. 23, 1988 [JP] Japan .................. 63-40166

[51] Int. Cl.$^4$ .......................... A61B 1/04; K04N 7/18
[52] U.S. Cl. .......................................... 358/98; 128/6
[58] Field of Search .................. 358/98, 229; 128/4, 128/6

[56] References Cited

U.S. PATENT DOCUMENTS 4,667,230 5/1987 Arakawa et al. .................. 358/98
4,774,568 9/1988 Matsuo ............................ 128/6 X

FOREIGN PATENT DOCUMENTS 0015117 1/1986 Japan ................................ 358/98

*Primary Examiner*—James J. Groody
*Assistant Examiner*—Victor R. Kostak
*Attorney, Agent, or Firm*—Armstrong, Nikaido, Marmelstein, Kubovcik & Murray

[57] ABSTRACT

The electronic endoscope apparatus of this invention is provided with a first endoscope apparatus having a solid state imaging device whereby an object image obtained from an observing window provided in the tip part of an insertable part inserted into a body cavity is formed and is converted to an electric signal to be output and a second endoscope apparatus having a solid state imaging device different from the solid state imaging device provided in the first endoscope apparatus in shape or number of pixels but the same in at least one pixel forming element. The first and second endoscope apparatus are connected to a video processing circuit and the electric signal output from the solid state imaging device is processed to be a video signal. The signal procesed by the video processing circuit is output to a displaying apparatus to display the object image.

17 Claims, 12 Drawing Sheets

ELECTRONIC ENDOSCOPE APPARATUS PROVIDED WITH A PLURALITY OF ENDOSCOPES HAVING SOLID STATE IMAGING DEVICES WITH AT LEAST ONE IDENTICAL PIXEL FORMING ELEMENT

BACKGROUND AND FIELD OF THE INVENTION

This invention relates to an electronic endoscope whereby a plurality of endoscopes can be used.

Recently, there is extensively used an endoscope whereby internal organs within a body cavity can be observed by inserting an elongate insertable part into the body cavity or various therapeutic treatments can be made by using treating tools inserted through a treating tool channel as required.

Various electronic endoscopes using a solid state imaging device such as a charge coupled device (CCD) are suggested.

Now, in a conventional video camera, there has been only one kind of pixel size of an imaging device (solid state imaging device) or a number of vertical pixels and horizontal pixels (which shall be mentioned as a pixel formation hereinafter).

However, recently, in an electronic endoscope, the observed parts are more and more manifold and the outside diameter allowed for the endoscope varies depending on the observed part. Particularly, when a comparatively large solid state imaging device such as is used for an electronic endoscope for lower digestive organs, such as the large intestine and small intestine, is used for an endoscope for observing a very fine diameter part such as a bronchus tip or vein, the endoscope will not be able to be made small enough in diameter. Therefore, with only one kind of solid state imaging device as in the past, various observed parts can not be well coped with.

Therefore, a solid state imaging device of a different size must be used in response to the observed part. In such a case, the number of pixels and sensitivity of the solid state imaging device will be different, therefore the switching of a circuit constant, such as an interpolating coefficient will be required and the adjustment of the gain by an automatic gain controlling circuit (which shall be abbreviated as an AGC hereinafter) will be complicated.

Therefore, in order to cope with the above mentioned problems, in the publication of a Japanese patent application laid open No. 179129/1986, there is disclosed a technique wherein a means of storing the information of various conditions, such as the type of endoscope, white balance, number of pixels of the solid state imaging device and sensitivity of the solid state imaging device, is provided on the endoscope body side and the connector on the endoscope body side is connected to the connector on the video processing part side so that the various conditions may be read into a reading-in apparatus on the video processing part side and may be transmitted to a control part to be automatically set.

However, there have been problems that, in the above mentioned conventional technique, so that many conditions may be stored so as to be able to correspond to a plurality of different endoscopes and further an adjustment matching the many conditions may be made automatically, the circuit scale will become large and the cost will become high.

OBJECT AND SUMMARY OF THE INVENTION

An object of the present invention is to provide an electronic endoscope apparatus wherein the characteristics of the pixel formation of a solid state imaging device are made the same with respect to two or more types of solid state imaging devices so that even an electronic endoscope with a different solid state imaging device may be used by switching the minimum circuit constants, the circuit scale may be small and the cost may be low.

The present invention comprises a first endoscope apparatus having a solid state imaging device whereby an object image obtained from an observing window provided in the tip part of an insertable part inserted into a body cavity is formed and is converted to an electric signal to be output. A second endoscope apparatus has a solid state imaging device which is different from the solid state imaging device provided in the first endoscope apparatus in the number of pixels but is the same in at least one pixel forming element. A video processing circuit is provided whereby the first and second endoscope apparatus can be connected and the electric signal output from the above mentioned solid state imaging device is processed to be a video signal. A displaying apparatus is provided whereby the signal processed by the video processing circuit is received and the above mentioned object image is displayed as a picture image.

BRIEF DESCRIPTION OF THE DRAWINGS

FIGS. 1 to 6 relate to the first embodiment of the present invention.

FIG. 1 is an explanatory view of the entirety of an electronic endoscope apparatus.

FIG. 3 is a schematic diagram of a video processing circuit.

FIG. 4 is a block diagram of an endoscope apparatus.

FIGS. 5a–5c are explanatory diagrams of a signal generating circuit of a pixel formation sensing means.

FIG. 6 is an explanatory diagram of a discriminating circuit of a pixel formation sensing means.

FIG. 8 is a block diagram of an endoscope apparatus.

FIG. 9 is a block diagram of the internal formations of a video processing means and video processing controlling means.

FIG. 10 is a block diagram of a picture image enlarging part.

FIG. 11 is a block diagram of a picture image contracting part.

FIG. 13 is an explanatory view showing the arrangement of color separating filters of a supplementary color system.

FIG. 14 is a block diagram showing the formation of an endoscope apparatus.

FIGS. 15 to 17 relate to the sixth embodiment of the present invention.

FIG. 15 is an explanatory view of an endoscope apparatus when an optical endoscope is fitted with an externally fitted TV camera.

FIG. 16 is an explanatory view of a pixel formation sensing means of an externally fitted TV camera.

DETAILED DESCRIPTION OF PREFERRED EMBODIMENTS OF THE INVENTION

The embodiments of the present invention shall be explained in the following with reference to the drawings.

FIGS. 1 to 6 show the first embodiment of the present invention.

Figure 1:
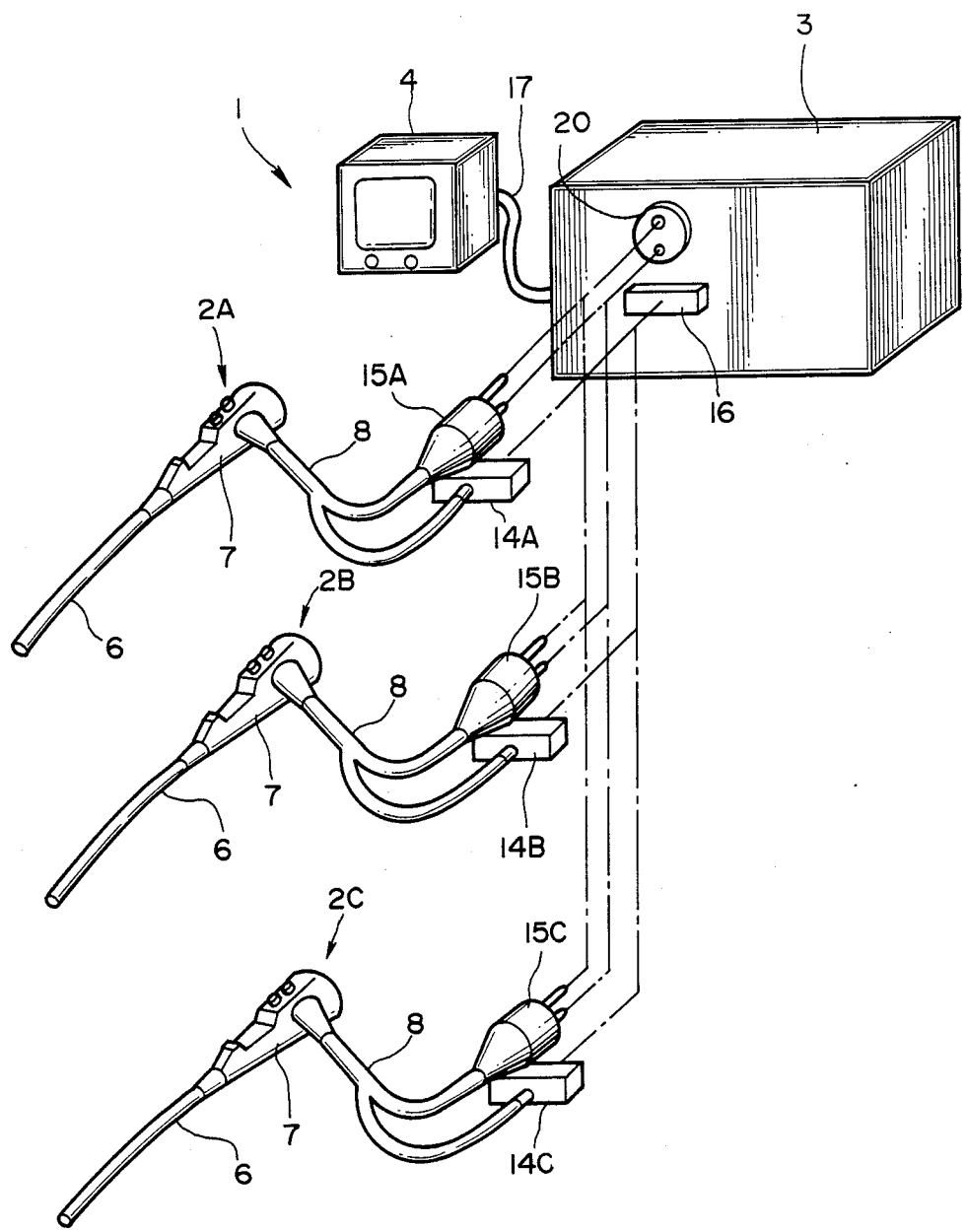

In FIG. 1, an electronic endoscope 1 comprises endoscopes 2A, 2B and 2C for different uses, a light source part to which this endoscope 2 (representing 2A, 2B or 2C) can be connected and which feeds an illuminating light to the endoscope 2, a control apparatus 3 having a signal processing part whereby the picture image signal delivered from the endoscope 2 is processed and a monitor 4 displaying on a picture surface the video signal output from this control apparatus 3.

Each above mentioned endoscope 2 comprises an elongate insertable part 6, a thick operating part 7 connected to this insertable part 6 on the rear end side and a light guide and signal cable 8 extended from the side of this operating part 7.

A light guide connector 15 (i.e., 15a, 15b and 15c) and signal connector 14 (i.e., 14a, 14b and 14c) are provided at the rear end of the above mentioned light guide and signal connector 8 and are connected respectively to a light guide connector receptacle 20 and signal connector receptacle 16.

The above mentioned control apparatus 3 is connected with the above mentioned monitor 4 through a signal cable 17.

Figure 2A:
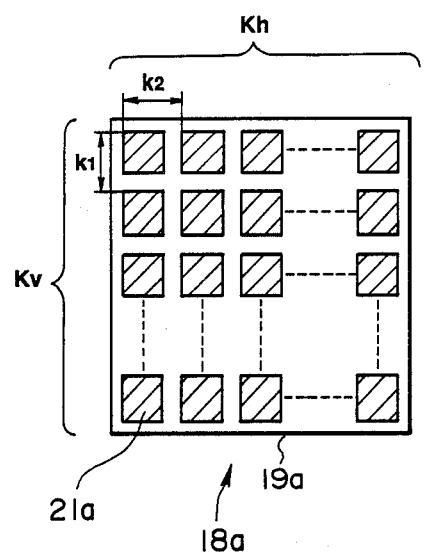
FIGS. 2a–2c are explanatory views of an imaging surface of a solid state imaging device.
Figure 2B:
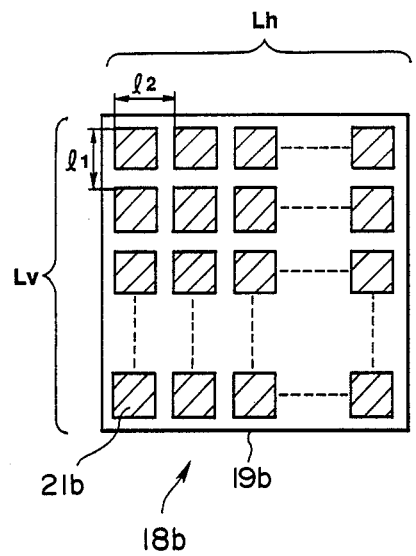
Figure 2C:
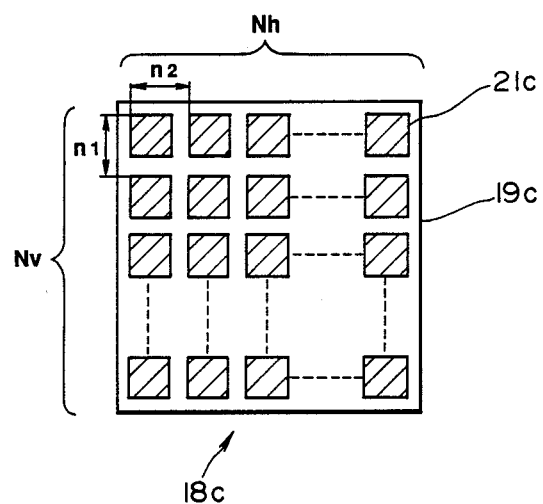

FIG. 2 shows a plurality of pixels 21a, 21b and 21c (represented by 21) forming imaging surfaces 19a, 19b and 19c (represented by 19) of solid state imaging devices 18a, 18b and 18c (represented by 18) provided in the three types of endoscopes 2A, 2B and 2C which can be connected to the above mentioned control apparatus 3.

If the respective sizes of the pixels 21 forming the above mentioned imaging surfaces 19 are $k_1$, $l_1$ and $n_1$ in the vertical direction and $K_2$, $L_2$ and $n_2$ in the horizontal direction, then $k_1 = k_2 = l_1 = l_2 = n_1 = n_2$. Also, if the numbers of pixels in the vertical direction are Kv, Lv and Nv and the number of pixels in the horizontal direction are Kh, Lh and Nh, then $Kv \neq Lv \neq Nv$ or $Kh \neq Lh \neq Nh$.

Figure 3:
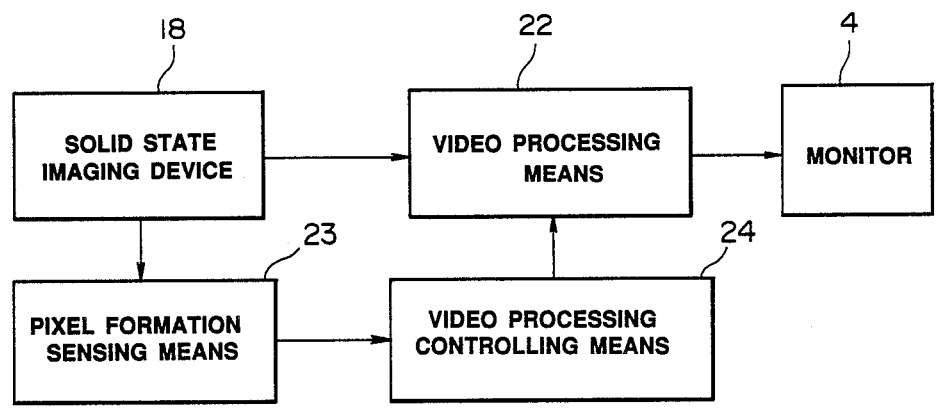

The object image imaged by the above mentioned solid state imaging device is processed to be a signal as in FIG. 3.

The electric signal photoelectrically converted by the solid state imaging device 18 is input into a video processing means 22. The ratio of the number of pixels in the vertical and horizontal directions of the solid state imaging device 18 is sensed by a pixel formation sensing means 23. This pixel formation sensing means 23 inputs a control signal showing the ratio of the number of pixels in the vertical and horizontal directions into a video processing controlling means 24. With this control signal input, the video processing controlling means 24 outputs to a video processing means 22 a synchronizing signal adapted to the solid state imaging device. The video processing means 22 produces a video signal by video-processing with the above mentioned synchronizing signal the electric signal containing the video information and outputs the video signal to the monitor 4.

A video processing circuit of a frame sequential type shall be explained in the following.

Figure 4:
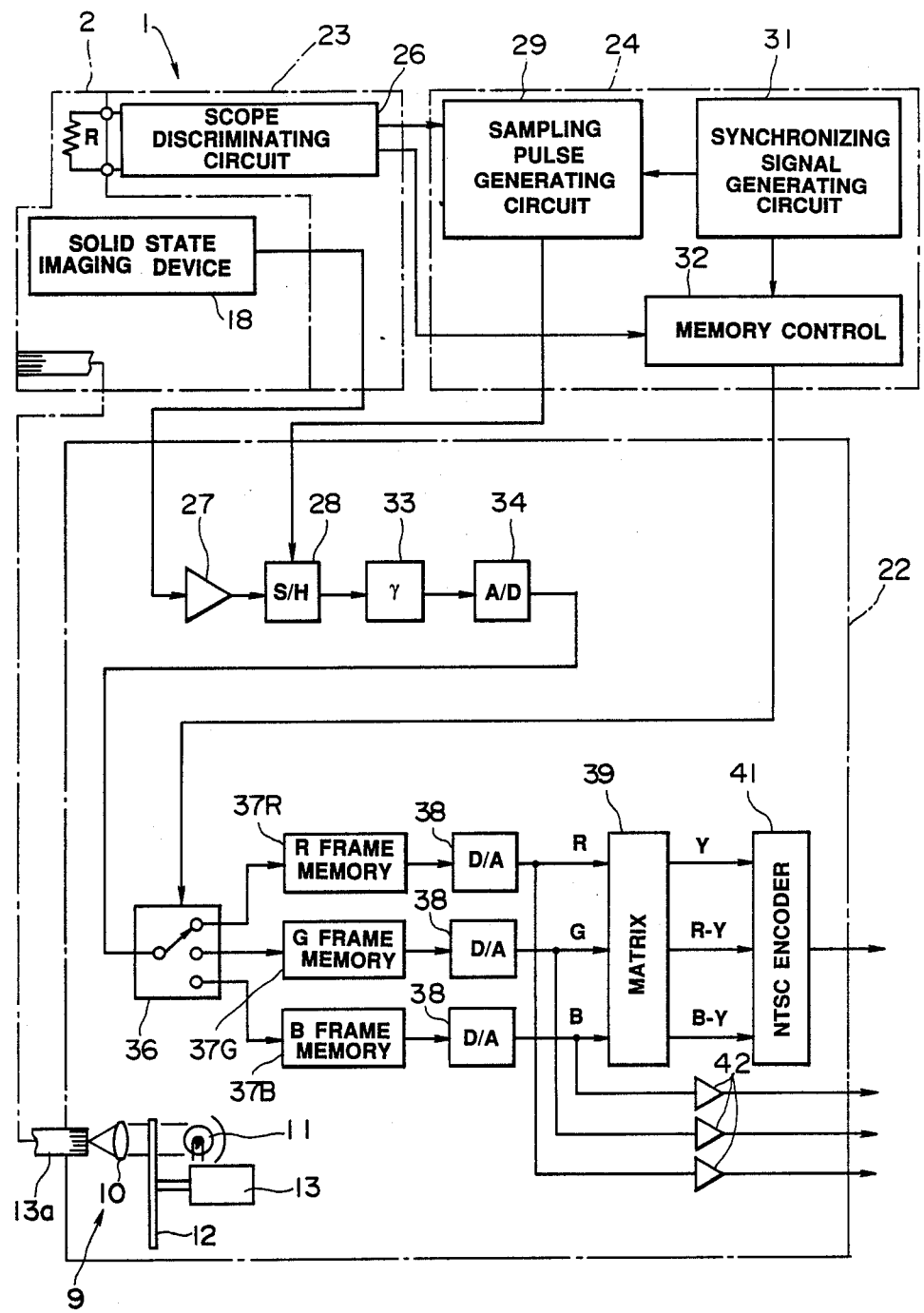

In FIG. 4, a light source part 9 is provided within the control apparatus 3 and comprises a light source lamp 11, a rotary filter 12 having color separating filters (not illustrated) separating in time series the illuminating light output from this light source lamp 11 into respective color light, for example, of red, green and blue. A motor 13 rotates and drives this rotary filter 12 and a condenser lens 10 condenses the color light having passed through the rotary filter and radiates the light onto the entrance end surface of the light guide 13a. The light having illuminated the object enters the solid state imaging device 18 as a reflected light. The object image formed on the imaging surface 19 of the solid state imaging device 18 is photoelectrically converted and is input as an electric signal into the video processing means 22. The solid state imaging device 18 has the number of pixels Kv, Lv and Nv in the vertical direction and the number of pixels Kh, Lh and Nh sensed by a scope discriminating circuit 26 as a pixel formation sensing means 23.

Figure 5:
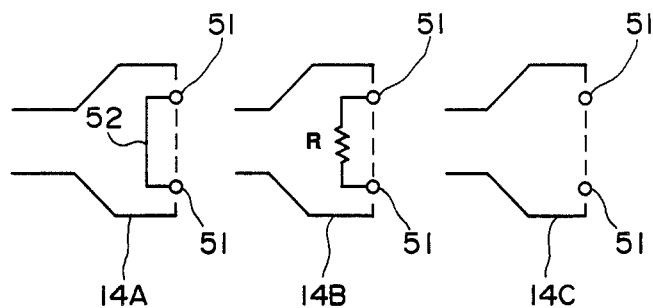
Figure 6:
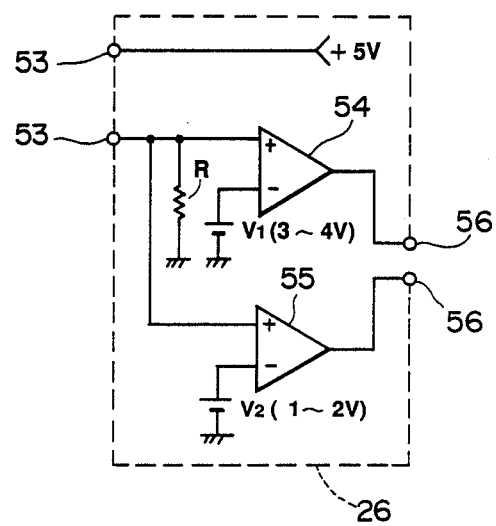

The scope discriminating circuit 26 forming the pixel formation sensing means 23 and the circuit outputting the signal for the discrimination are formed as in FIGS. 5 and 6.

As shown in FIG. 5, two terminals 51 outputting signals for sensing the number of pixels of the endoscope 2 are provided in each of the signal connectors 14A, 14B and 14C (the other signal terminals are omitted). The control apparatus 3 discriminates the resistance value between the two terminals 51 in the scope discriminating circuit 26 and outputs the discriminated results to the above mentioned sampling pulse generating circuit 29.

In case there are three types of endoscopes 2 as in this embodiment, in the connector 14A of the endoscope 2A, the two terminals 51 are short-circuited by a lead wire 52, in the connector 14B of the endoscope 2B, the two terminals 51 are connected with each other through a resistance R, for example, of 220Ω and, in the connector 14C of the endoscope 2C, the two terminals 51 are open therebetween and are connected with an equivalently infinite resistance.

On the other hand, as shown in FIG. 6, the scope discriminating circuit 26 has input ends 53 of the signal connector receptacle 16. One input end 53 is connected to a current source end of +5V and the other input end 53 is connected to non-inverted input ends of comparators 54 and 55 and is grounded through a resistance R, for example of 200Ω.

On the other hand, a voltage $V_1$, for example, of 3 to 4 V is applied to the inverted input end of the comparator 54 by a reference voltage source and a voltage $V_2$, for example, of 1 to 2 V is applied to the inverted input end of the other comparator 55 by the reference voltage source. Thus, the signals of 2 bits output from the output ends 56 of the respective comparators 54 and 55 become control signals output in response to the pixel formation of the endoscope 2.

In this formation, for example, when the connector 14A of the endoscope 2A is connected, the respective outputs of the comparators 54 and 55 to be control signals will be "H" and "H", when the connector 14B of the endoscope 2B is connected, the outputs of the comparators 54 and 55 will be "L" and "H" and, when the connector 14C of the endoscope 2C is connected, the outputs of the comparators 54 and 55 will be "L" and "L".

The scope discriminating circuit 26 inputs a control signal showing a ratio of the number of pixels as is mentioned above into a sampling pulse generating circuit 29 within the video processing controlling means 24 and the sampling pulse generating circuit 29 generates a sampling pulse. This sampling pulse generating circuit 29 inputs into the solid state imaging device 18 a synchronizing signal from a synchronous signal generator 31 controlling a CCD driver (not illustrated) outputting a driving clock. This synchronous signal generator 31 inputs the synchronous signal also into a memory controlling circuit 32 into which a control signal corresponding to the ratio of the number of pixels of the scope discriminating circuit 26 is input. The scope discriminating circuit 26 outputs to a CCD driver (not illustrated) a control signal showing the ratio of the number of pixels.

The electric signal input into the video processing means 22 is amplified by a pre-amplifier 27 and is input into a sample holding circuit 28 holding samples by sample holding pulses input from the above mentioned sampling pulse generating circuit 29.

After the sample is held, the signal has γ corrected by a γ correcting circuit 33 and is converted to a digital signal by an A/D converter 34. The signals imaged under the frame sequential illumination of R, G and B through a multiplexer 36 switched by the signal of the above mentioned memory controlling circuit 32 are written into an R frame memory 37R, G frame memory 37G and B frame memory 37B. The signal data written into these respective frame memories 37R, 37G and 37B are simultaneously read out, are converted respectively to analogue color signals R, B and G by D/A converters 38, are output to a matrix circuit 39 and are, on the other hand, output to the monitor 4 through buffers 42 as three primary color signals R, G and B. The matrix circuit 39 produces luminance signal and color difference signals R-Y and B-Y which are input into an NTSC encoder 41 and a composite video signal of an NTSC system is output to the monitor 4.

The operation of the electronic endoscope apparatus 1 formed as mentioned above shall be explained.

The solid state imaging devices 18a, 18b and 18c have the pixel number ratio sensed by the scope discriminating circuit 26 and outputs a control signal showing this pixel number ratio to the sampling pulse generating circuit 29, memory controlling circuit 32 and a CCD driver (not illustrated). The CCD driver generates a number of driving pulses adapted to the number of pixels and applies them to the solid state imaging device 18 and the sampling pulse generating circuit 29 generates sampling pulses of a timing which can hold samples of the video components from the electric signal read out by the driving pulses. Further, the memory controlling circuit 32 writes color signals illuminated by the respective color light into the respective frame memories 37R, 37G and 37B.

As mentioned above, in this embodiment, the size of the pixels 21 in the vertical and horizontal direction of each solid state imaging device 18 is made the same. Therefore, the gain for the sensitivity of pixels produced by the difference in the size of the pixels need not be adjusted and the electric signal output from each solid state imaging device 18 can be processed by only adjusting the variation in the number of pixels.

Further, the resolutions of the respective solid state imaging devices 18 can be made to coincide with each other.

As the pixels 21 forming the imaging surface 19 of each solid state imaging device are square, the pixel pitch in the vertical and horizontal directions is the same and the resolution in the vertical direction and horizontal direction of one pixel is equal to all other pixels. Thus, in an electronic endoscope wherein the solid state imaging device 18 is directed in all directions and the perpendicular direction of the object and the vertical direction of the solid state imaging device 18 do not always coincide with each other, in any case, the resolution in the vertical and horizontal directions of the displayed picture image can be made equal to each other.

Further, the pixel 21 is square and is therefore very adaptable to apply a picture image process such as measuring on the displaying picture image the size of any part of the imaged object.

In this embodiment, three types of solid state imaging devices 18 are used but the embodiment is not limited to three and may be two or four or more types.

Figures 7A, 7B:
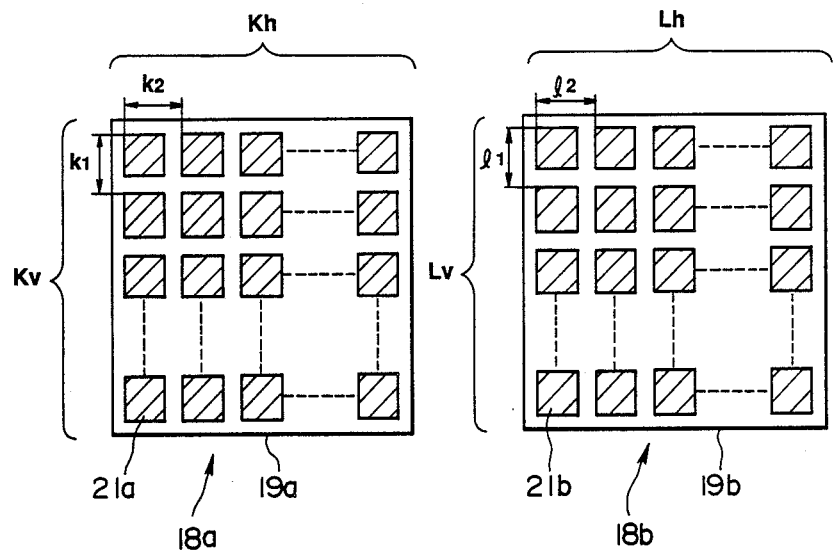
FIGS. 7a–7c relate to the second embodiment of the present invention and is an explanatory view of an imaging surface of a solid state imaging device.
Figure 7C:
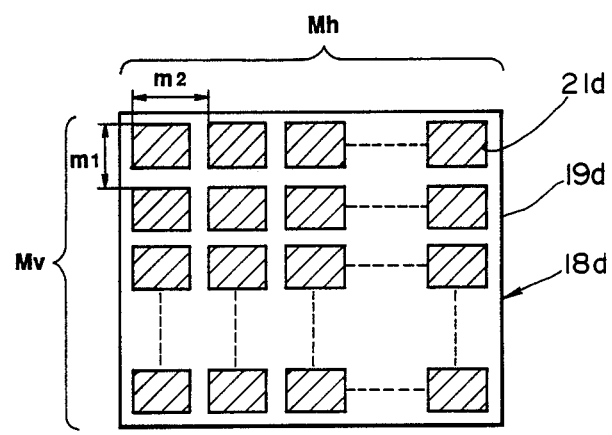

FIG. 7 relates to the second embodiment of the present invention and is an explanatory view of an imaging surface of a solid state imaging device.

This embodiment is of the endoscopes 2A and 2B provided with the solid state imaging devices 18a and 18b described in the first embodiment and a newly added endoscope 2D provided with a solid state imaging device 18d. If the size in the vertical direction of the pixel 21d forming the imaging surface 19d of this solid state imaging device 18d is represented by $m_1$, the size in the horizontal direction is represented by $m_2$, the number of pixels in the horizontal direction is represented by $M_h$ and the number of pixels in the vertical direction is represented by $M_v$, then $k_1 \neq l_1 \neq m_1 \neq k_2 \neq l_2 \neq m_2$. The respective number of pixels are $K_v \neq L_v \neq M_v$ or $K_h \neq L_h \neq M_h$ and the number of pixels of the solid state imaging device 18d are $M_h = M_v$.

The video processing circuit of this embodiment shall be explained with reference to FIG. 3.

The above mentioned solid state imaging device 18d is different from the other solid state imaging devices 18a and 18b in the size of the pixel 21 and therefore in the signal level of the photoelectrically converted electric signal. Therefore, in order to adjust this different signal level, an automatic gain controlling circuit is provided within the video processing means 22. In this automatic gain controlling circuit, a control signal corresponding to the sensitivity of the solid state imaging device 18d sensed in advance by the picture image formation sensing means 23. The control signal is input from the video signal processing controlling means 24 so as to be the optimum gain. The electric signal adjusted in the signal level is processed by the video processing circuit described in the first embodiment and is displayed on the picture surface of the monitor 4.

As mentioned above, according to this embodiment, as the solid state imaging device 18d is different from the other solid state imaging devices 18a and 18b in the size of the pixel but has the same number of pixels in the vertical and horizontal directions, the resolving power in the vertical and horizontal directions can be made equal to each other.

The other formations, operations and effects are the same as in the first embodiment.

In this embodiment, the solid state imaging devices 18 are of three types and the solid state imaging devices 18 in which the size of the pixel 21 is the same are of two types but are not limited to these and may be of two or more types.

Figure 8:
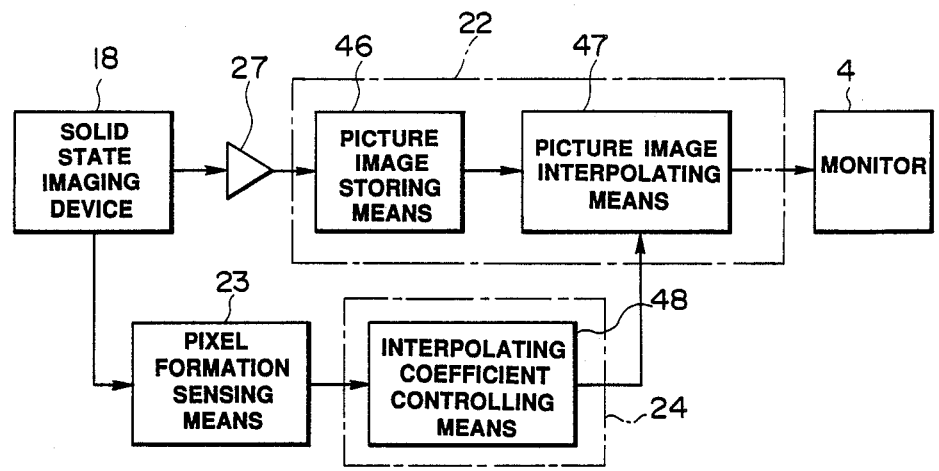
FIGS. 8 to 11 relate to the third embodiment of the present invention.
Figure 9:
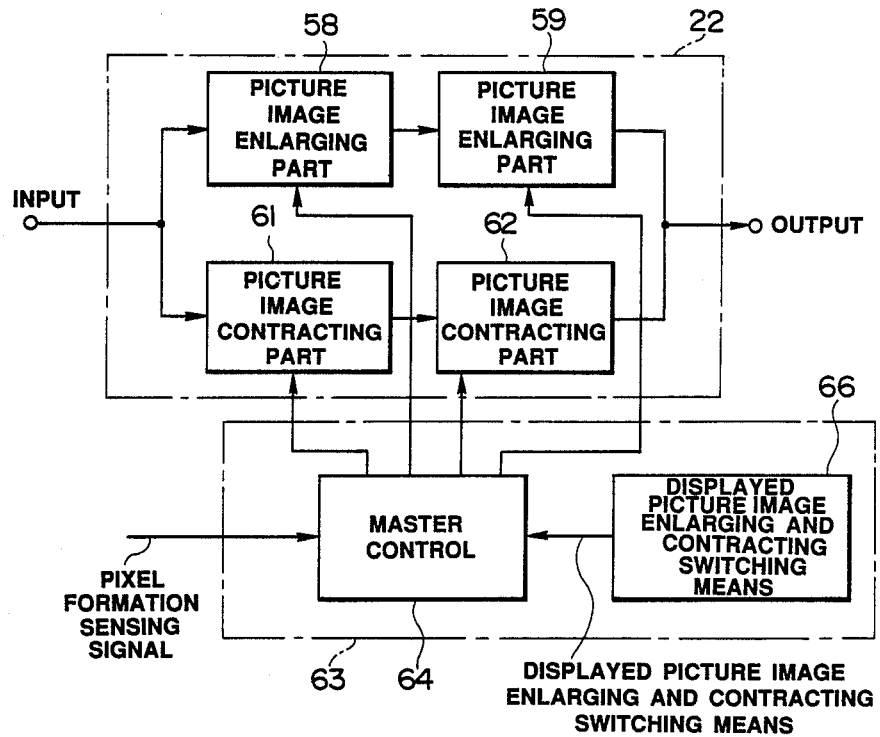
Figure 10:
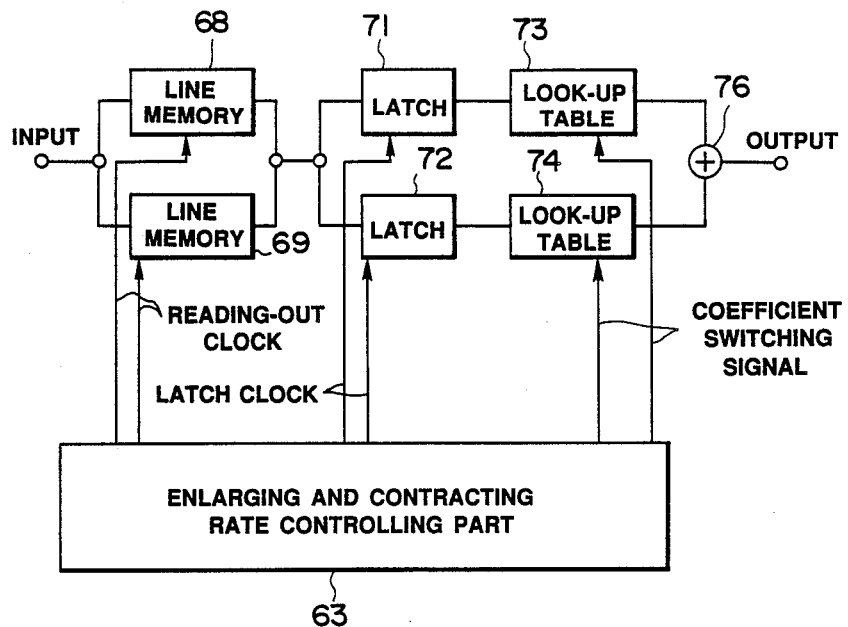
Figure 11:
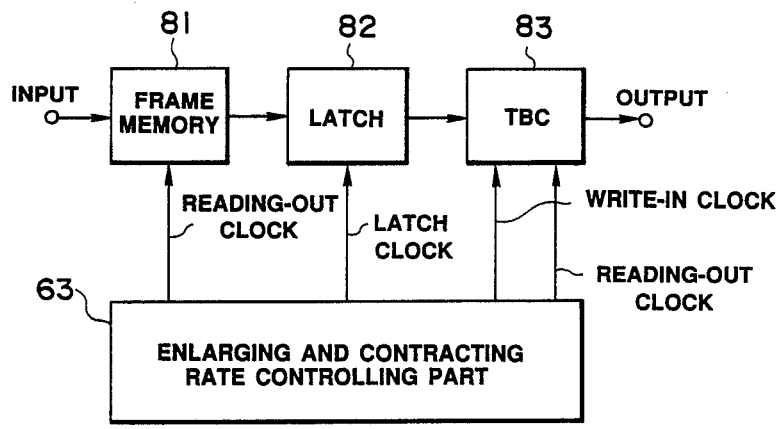

FIGS. 8 to 11 relate to the third embodiment of the present invention. FIG. 8 is a block diagram of an endoscope apparatus. FIG. 9 is a block diagram of the internal formations of a video processing means and video processing collections means. FIG. 10 is a block diagram of a picture image enlarging part. FIG. 11 is a block diagram of a picture image constructing part.

The present invention shall be explained with reference to FIGS. 2(a) and (b) and FIGS. 8 to 11.

In FIG. 2(a) and (b), in this embodiment, the ratio of the number of pixels of the solid state imaging devices 18a and 18b is $K_v:L_v = K_h:L_h$ and the ratio of the number of pixels in the vertical and horizontal directions is the same.

In FIG. 8, the electric signal converted by the solid state imaging device 18 is amplified by the pre-amplifier 27, is converted to a digital signal and is input into the picture image processing means 22. The number of pixels of the solid state imaging device 18 is sensed by the pixel formation sensing means 23 and a control signal showing the number of pixels is generated and is input into an interpolating coefficient controlling means 48.

The above mentioned picture image processing means 22 is provided with a picture image storing means 46 formed, for example, of a plurality of lines memories and one line each is written into this line memory. The signal data written into this picture image storing means 46 is read out, is input into a picture image interpolating means 47, is enlarged in the vertical and horizontal directions and is interpolated. This picture image interpolating means 47 has the optimum interpolating coefficient and enlarging rate set by the above mentioned interpolating coefficient controlling means 48 and has the enlarging rate and interpolating rate of the picture image controlled.

The video signal interpolated and enlarged by the above mentioned picture image interpolating means 47 is then processed by the video processing circuit described in the first embodiment and is displayed on the picture surface of the monitor 4.

In this embodiment, when $K_h > L_h$, the large solid state imaging device 18a is used for observing lower digestive organs such as, for example, the large intestine and small intestine and the small solid state imaging device is used for very fine parts such as veins and bronchi, the pixel number difference will be likely to become considerably large. Therefore, if both are driven by the same driving method, the picture image displaying area of the solid state imaging device 18b will likely become much smaller than that of the solid state imaging device 18a. Therefore, generally, a picture image storing means 46 shown in FIG. 8 and a picture image interpolating means 47 interpolating a video signal of pixels of a plurality of lines from the picture image storing means 46 are provided within the video processing means 22 to enlarge the picture image.

The most important problem is to make an electronic endoscope small in diameter. However, in fact, even the solid state imaging device 18 for the lower digestive organs for which a comparatively thick diameter is allowable must be made small in the diameter in order to reduce the pain to the patient. Therefore, in the electronic endoscope, it is necessary to more or less electronically enlarge the picture image. In such a case, unless an interpolation is applied, a mosaic-like picture image will be made. Therefore, an interpolation is applied as described above. In the electronic endoscope 1 in which a plurality of solid state imaging devices 18 can be used, if the numbers of pixels in the vertical and horizontal directions of the respective solid state imaging devices 18 are irregular, whenever the solid state imaging device 18 is switched, the enlarging rate and interpolating degree will have to be switched independently vertically and horizontally and it will be very complicated. Now, according to this embodiment, as the ratios of the number of pixels in the vertical and horizontal directions of the respective solid state imaging devices 18 are made the same, an enlargement and interpolation of the picture image can be made at the same rate in the vertical direction and horizontal direction and therefore the circuit is simple and can be formed at a low cost.

The other formations, operations and effects are the same as in the first embodiment.

In this embodiment, the ratio of the number of pixels of one set of the solid state imaging devices 18 is made the same but, without being limited to this, two or more sets may be made the same. Further, the ratio of the number of pixels in the vertical and horizontal directions of three or more types of solid state imaging devices 18 may be made the same.

Further, the interpolating coefficient controlling means 48 and video processing means 22 may be formed as shown in FIGS. 9 and 11 so that the picture image may be not only enlarged but also contracted.

In FIG. 9, the video signal obtained from the solid state imaging device 18 is input into the video processing means 22. This input video signal is branched and one branch is enlarged and interpolated in the vertical or horizontal direction by the a first picture image enlarging part 58. The video signal from this first picture image enlarging part 58 is enlarging part 59 in the direction vertical to the direction in which it was enlarged by the above mentioned first picture image enlarging part 58. The other branch of the video signal is contracted in the vertical or horizontal direction by a first picture image contracting part 61. The video signal from this first picture image contracting part 61 is contracted by a second picture image contracting part 62 in the direction vertical to the direction in which it was contracted by the above mentioned first picture image contracting part 61.

The first and second picture image enlarging parts 58 and 59 and the first and second picture image contracting parts 61 and 62 form the video processing means 22.

The first and second picture image enlarging parts 58 and 59 and the first and second picture image contracting parts 61 and 62 are controlled in the picture image enlarging rate, interpolating rate and contracting rate by a master control 64 provided in an enlarging and contracting rate controlling part 63 as the video processing controlling means 24. The master control 64 receives a pixel formation sensing signal from the scope discriminating circuit 26 sensing the pixel formation of the solid state imaging device 18 and delivers an enlarging and contracting rate controlling signal corresponding to the picture image formation to the above mentioned picture image enlarging parts 58 and 59 and picture image contracting parts 61 and 62. Further, the master control 64 receives a control signal from a displayed picture image enlarging and contracting switching means 66 which can select the size of the displayed picture image by an external input means such as a push switch. The displayed picture image enlarging and contracting switching signal from this displayed picture image enlarging and contracting switching means 66 is input into the master control 64. The above mentioned master control 64 operates the pixel formation sensing signal from the above mentioned scope discriminating circuit 26 and the displayed picture image enlarging and contracting switching signal from the above mentioned displayed picture image enlarging and contracting switching means 66 and outputs an enlarging rate controlling signal to the picture image enlarging parts 58 and 59 or a contracting rate controlling signal to the picture image contrating parts 61 and 62 so that the enlarging or contracting rate may be proper.

An example of the picture image enlarging part which is the first picture image enlarging part 58 or the second picture image enlarging part 59 shall be explained in the following with reference to FIG. 10.

This horizontal picture image enlarging part comprises two line memories 68 and 69 in which a digital video signal is input and a writing-in operation and reading-out operation are alternately switched, two latches 71 and 72 inputting the outputs of the above mentioned line memories 68 and 69, look-up tables 73 and 74 multiplying the outputs of the above mentioned latches 71 and 72 respectively by interpolating coefficients $\alpha ij$ and $\beta ij$ ($\alpha ij \leq 1$, $\beta ij \leq 1$, $\alpha ij + \beta ij = 1:1$ and j is an integer) and an adder 76 adding and outputting the outputs of these look-up tables 73 and 74. The above mentioned line memories 68 and 69 are alternately written in at intervals of one line and are read out as synchronized with the reading-out clock signal from the enlarging and contracting rate controlling part 63. Only the signals synchronized with the latch clocks from the above mentioned enlarging and contracting rate controlling part 63 are stored in the latches 71 and 72 continue to be held until the next latch clocks are transmitted from the above mentioned enlarging and contracting rate controlling part 63. The outputs of the above mentioned latches 71 and 72 are multiplied by the interpolating coefficients $\alpha ij$ and $\beta ij$ in the look-up tables 73 and 74. These interpolating coefficients $\alpha ij$ a $\beta ij$ are switched for each pixel by the coefficient switching signals from the above mentioned enlarging and contracting rate controlling part 63.

An example of the first picture image contracting part 61 or the second picture image contracting part 62 shall be also explained with reference to FIG. 11.

The video signal for one frame obtained from the solid state imaging device 18 is stored in a frame memory 81 and is read out for only the required scanning lines with the reading-out clock output from the enlarging and contracting rate controlling part 63 at a timing corresponding to the picture image contracting rate to thin out the scanning lines. The video signal thinned in the vertical direction by the frame memory 81 is delivered to a latch 82 which reads out the video signal at a pixel unit according to the latch clock output in response to the picture image contracting rate from the enlarging and contracting rate controlling part 63 and thins the video signal in the horizontal direction. The video signal thinned in the horizontal direction by the latch 82 has a time axis corrected by a time base corrector (TBC) 83 to obtain a contracted video signal.

Figure 12A:
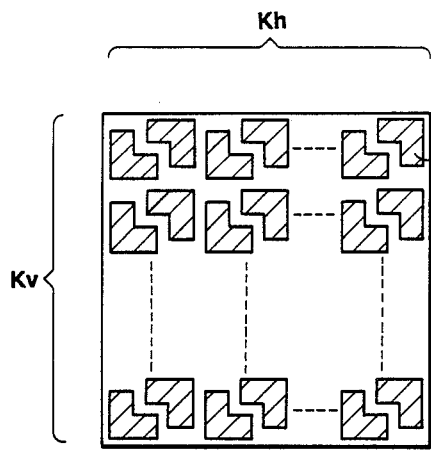
FIGS. 12a–12c relate to the fourth embodiment of the present invention and is an explanatory view of an imaging surface of a solid state imaging device.
Figure 12B:
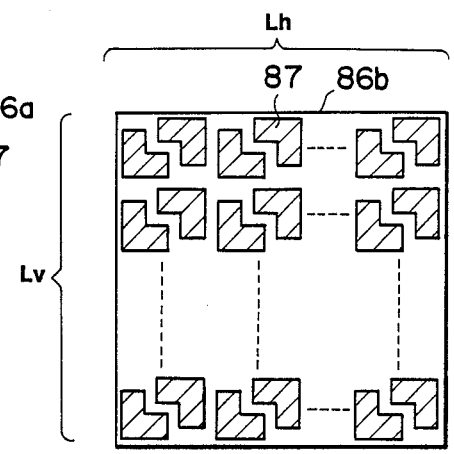
Figure 12C:
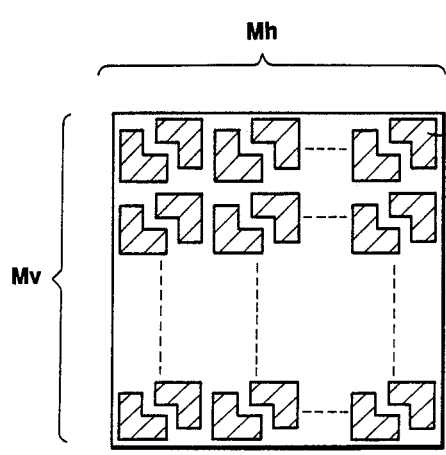

FIG. 12 relates to the fourth embodiment of the present invention and is an explanatory view of an imaging surface of a solid state imaging device.

This embodiment is an example of using solid state imaging devices 86a, 86b and 86c in which the shape and area of the pixel are the same. The respective solid state imaging devices 86a, 86b and 86c are different from one another in the vertical or horizontal direction in the number of pixels on either one side but are common in shape and dimension of the pixel 87 and $K_h \neq L_h$ or $K_v \neq L_v$, $L_h \neq M_h$ or $Ll_v \neq M_v$, $M_h \neq K_h$ or $M_v \neq K_v$.

The other formations are the same as in the first embodiment.

In this embodiment, the pixel 87 is L-shaped and is in a close position relation with the peripheral pixel 87 and therefore the picture image obtained by the interpolation is better than a conventional rectangular pixel. If this embodiment is applied to a simultaneous type imaging apparatus using, for example, a color mosaic filter, few false colors will appear.

Also, in this embodiment, since the shape and dimension of the pixel 87 are the same, in any solid state imaging device 86, for signal processing, the gain for the sensitivity of the pixel 87 need not be adjusted and the electric signal output from each solid state imaging device can be processed by only adjusting the variation of the number of pixels.

The shape of the pixel of the solid state imaging device 86 may be any other shape and may be circular or octagonal.

Figure 13:
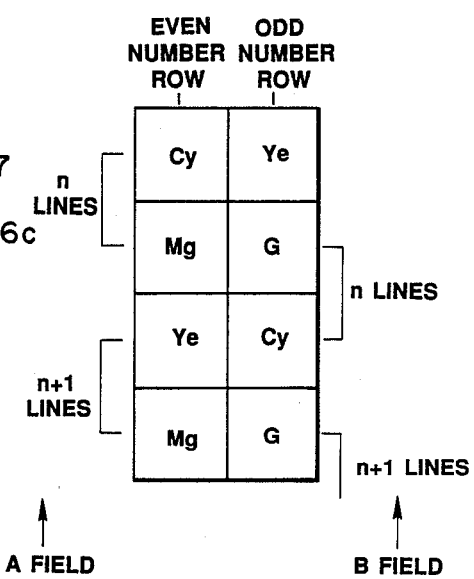
FIGS. 13 and 14 relate to the fifth embodiment of the present invention.
Figure 14:
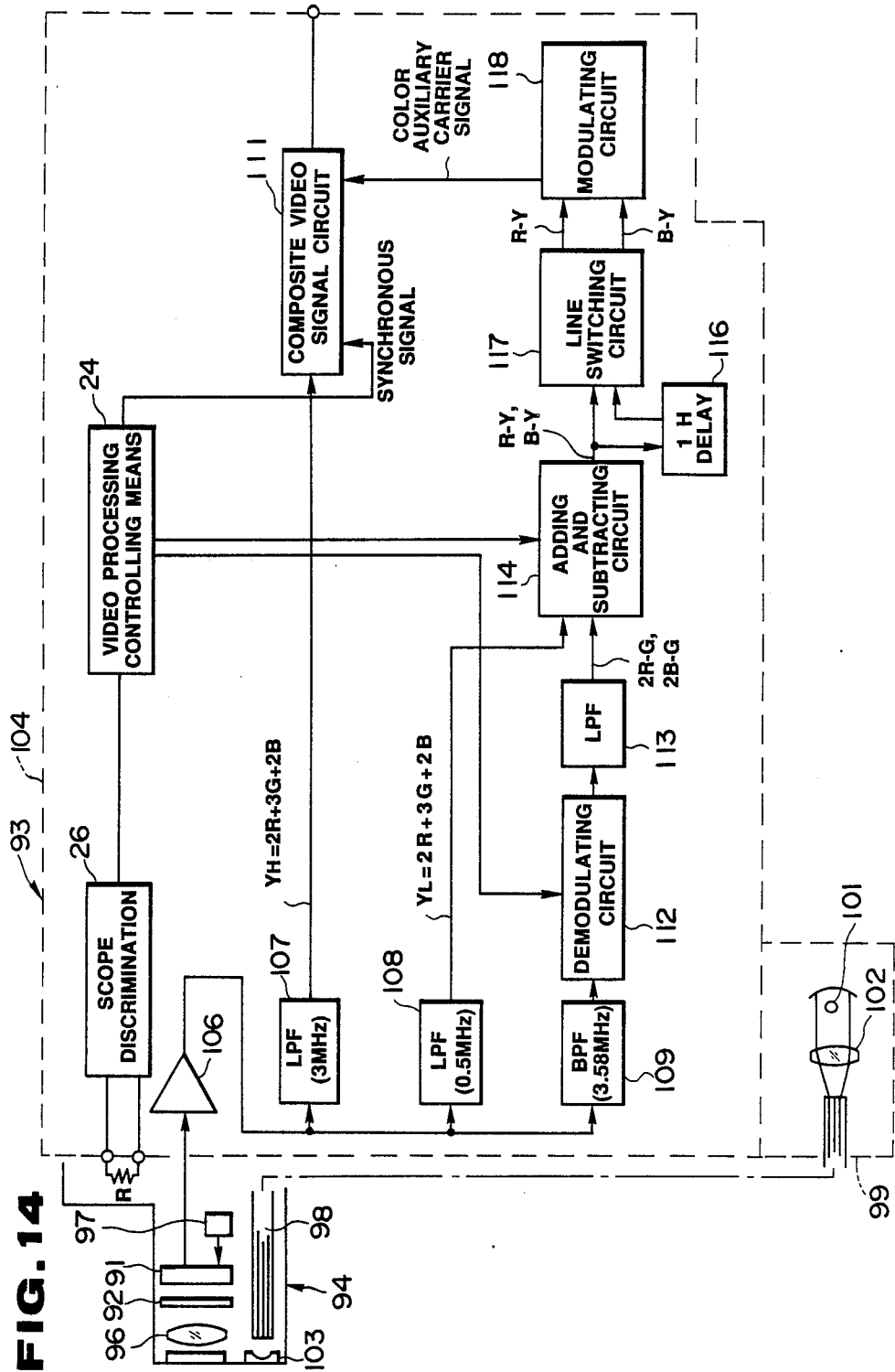

FIGS. 13 and 14 relate to the fifth embodiment of the present invention. FIG. 13 is an explanatory view showing the arrangement of color separating filters of a supplementary color sytem. FIG. 14 is a block diagram showing the formation of an endoscope apparatus.

This embodiment is an application of the present invention to a simultaneous type electronic endoscope 93 having a color separating filter 92 arranged in front of a solid state imaging device 91.

The above mentioned endoscope 93 is provided with an image forming objective lens system 96 on the tip side of an elongate insertable part 94 and the solid state imaging device 91 driven by a driving circuit 97 is arranged in the focal plane of this objective lens system 96.

A light guide 98 formed of a flexible fiber bundle as an illuminating light transmitting means is inserted through the above mentioned insertable part 94, is extended out of the endoscope 93 and is connected to a light source part 99 in which the white color light of a light source lamp 101 is condensed by a condenser lens 102 and is radiated on the entrance end surface of the light guide 98. The illuminating light from the above mentioned light source part 99 passes through the light guide 98, is emitted from the exit end surface of this light guide 98 and illuminates an object through a light distributing lens system 103.

The reflected light from the above mentioned object comes to the above mentioned solid state imaging device 91 to form an optical image by the objective lens system 96. The output signal of the solid state imaging device 91 is amplified by a pre-amplifier 106 within a signal processing part 104 and is fed to low-pass filters (LPF's) 107 and 108 and a band-pass filter 9 (BPF) 109. In case the reading-out frequency of the solid state imaging device 91 is 7.16 MH$_z$, the passing bands of the LPF's 107 and 108 will be of respectively 3 MH$_2$ and 0.5 MH$_z$, the central frequency of the BPF 109 will be 3.58 MH$_z$ and the band width will be of about 1 MH$_z$. The color array of the color separating filter 92 is as in FIG. 13 and therefore a luminance signal of the composition of (Cy-+Ye)+(Mg+G)=(B+G+R+G)+(R+B+G)=2R-+3G+2B is obtained. A wide band luminance signal Y$_H$ and narrow band luminance signal Y$_L$ are obtained respectively from the LPF's 107 and 108. The wide band luminance signal Y$_H$ output from the LPF 107 is input into a composite video signal circuit 111. The output of the BFF 109 is input into an adding and subtracting circuit 114 through a demodulating circuit 112 and LPF 113. In the demodulating circuit 112, the output of an even number row reduces the output of an odd number row and the following color difference signals are alternately output as color difference signals, in one line represented as an n line in FIG. 13, a (Cy+Mg)-−(Ye+G)=(B+G+R+B)−(R+G+G)=2B−G signal is obtained and, in the other line represented as an n+1 line, a (Ye+Mg)−−(Cy+G)=(R+G+R+B)−(B+G+G)=2R−G signal is obtained. The 2B=G and 2R−G signals obtained here are equivalent respectively to B−Y and R−Y. The narrow band luminance signal Y$_L$ output from the LPF 108 is input also into the adding and reducing circuit 114. The color difference signals required to obtain a composite video signal are R−Y and B−Y signals and therefore, in the adding and subtracting circuit 114, the color difference signals and narrow band luminance signal Y are multiplied by a proper coefficient and are added and the color difference signals R−Y and B−Y are output. Here, the demodulating circuit 112 outputs alternately color difference signals 2R−G and 2B−Y in each line and therefore, from the adding and reducing circuit 114, also, color difference signals R−Y and B−Y are alternately output in each line. Therefore, the output signal of the adding and reducing circuit 114 is made simultaneous by using a 1 H (one horizontal scanning period) delay circuit 116 and line switching circuit 117. That is to say, the color difference signal of each line is delayed by 1 H period and is output from a line switching circuit 117 together with the color difference signal of the next line. The color difference signals R−Y and B−Y output from this line switching circuit 117 are modulated (3.58 MH$_z$) by a modulating circuit 118 and a color auxiliary carrier signal is produced and is fed to the above mentioned composite video signal circuit 111 which generates a composite video signal on the basis of this color auxiliary carrier signal, the wide band luminance signal Y$_H$ output from the LPF 107 and a synchronized signal.

A timing signal adapted to the solid state imaging device 91 provided in the endoscope 93 is input into the above mentioned demodulating circuit 112 and adding and subtracting circuit 114 from the video signal processing controlling means 24 and a synchronizing signal is input into the composite video signal circuit 111 from this video signal controlling means 24. In the demodulating circuit 112, a subtraction is made on the basis of this timing signal and a color difference signal is output. In the adding and reducing circuit 114, the color difference signal and narrow band luminance signal Y$_L$ are added on the basis of this timing signal.

In the video signal controlling means 24, the information signal relating to the pixel formation of the solid state imaging device 91 provided in the endoscope 93 is input from the scope discriminating circuit 26 described in the first embodiment and the above mentioned timing signal adapted to the pixel formation of this solid state imaging device 91 and the synchronizing signal are output. Further, to the scope discriminating circuit 26 is connected a resistance of a resistance value showing the pixel formation of the solid state imaging device 91 provided in the endoscope 93 and the pixel formation is discriminated by this resistance value.

In this embodiment, the present invention is applied to an endoscope of a simultaneous type imaging system and the same effects as of the first embodiment can be obtained by the above mentioned formation.

Figure 15:
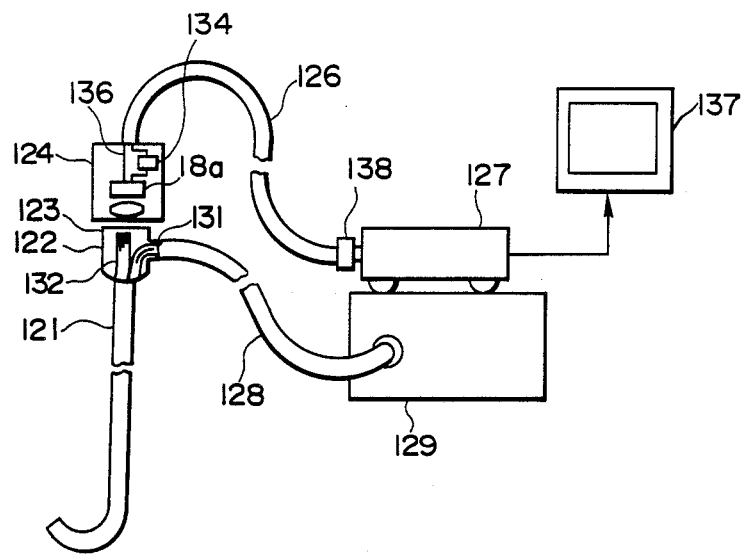
Figure 16:
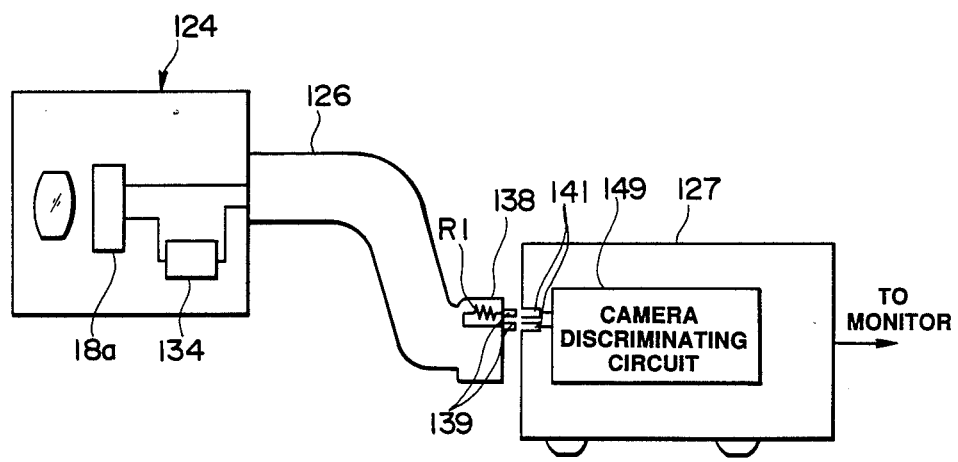
Figure 17A:
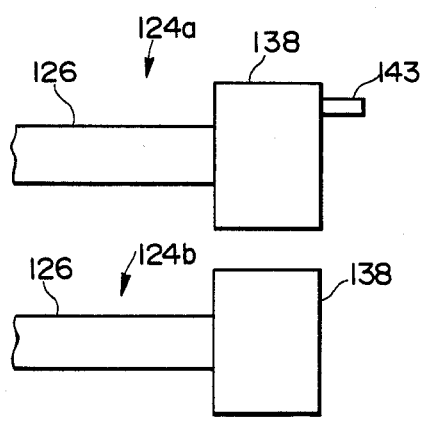
FIGS. 17a and 17b are explanatory views of a pixel formation sensing means of another externally fitted TV camera.
Figure 17B:
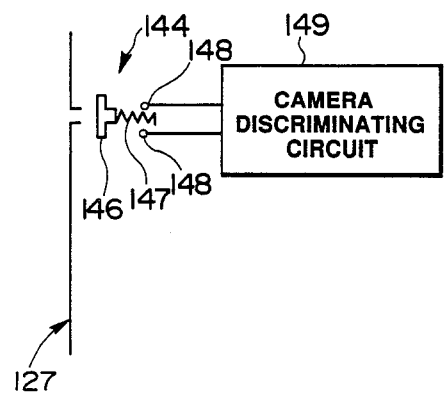

FIGS. 15 to 17 relate to the sixth embodiment of the present invention. FIG. 15 is an explanatory view of an endoscope apparatus in which an optical endoscope is fitted with an externally fitted TV camera. FIG. 16 is an explanatory view of a pixel formation sensing means of an externally fitted TV camera. FIG. 17 is an explanatory view of a pixel formation sensing means of another externally fitted TV camera.

This embodiment is an application of the present invention to an externally fitted TV camera fitted to an optical endoscope.

In FIG. 15, an externally fitted TV camera 124 having a solid state imaging device 18a of the pixel formation described, for example, in the first embodiment is removably fitted to an eyepiece part 123 provided at the rear end of an operating part 122 of an optical endoscope 121 and is connected to a camera controlling unit 127 through a signal cable 126 extended out of the rear end part. A flexible universal cable 128 is extended out of the side of the operating part 122 and is connected with a light source apparatus 129. The illuminating light output from the light source apparatus 129 is transmitted through a light guide 131 inserted through the universal cable 128 and is emitted from the tip part of the optical endoscope 121 to illuminate an object. The light returning from the object is transmitted through an image guide 132 and the object image is transmitted to the eyepiece part 123. This object image is formed by an image forming lens on the imaging surface of the solid state imaging device 18a provided within the externally fitted TV camera 124. The formed optical image is photoelectrically converted and is input as an electric signal into a signal processing circuit 134. The picture image signal produced by the signal processing circuit 134 is delivered to the camera controlling unit 127 through a plurality of signal lines 136 inserted through the signal cable 126. A plurality of current source lines (not illustrated) which can feed a current to the externally fitted TV camera 124 from the camera controlling unit side are also inserted through this signal cable 126.

In the above mentioned camera controlling unit 127, the picture image signal is converted, for example, to an NTSC composite video signal which is output to a TV monitor 137 and the object image is displayed on the picture surface.

A connector 138 provided at the end of the signal cable 126 of the externally fitted TV camera 124 and connectable to the camera controlling unit 127 is provided with a resistance R$_1$ generating a signal showing the pixel formation of the solid state imaging device 18a of this externally fitted TV camera 124.

In FIG. 16, the connector 138 of the externally fitted TV camera 124 is provided with pins 139 connected to both ends of the above mentioned resistance $R_1$ and projecting rearward. When the connector 138 is connected to the camera controlling unit 127, these pins 139 will be able to be electrically connected with pin receptacles 141 provided in this camera controlling unit 127. A camera discriminating circuit 149 of the same formation as the scope discriminating circuit 26 described in the first embodiment is connected to the pin receptacles 141 to discriminate the pixel formation of the solid state imaging device 18a provided in the externally fitted TV camera 124. The pixel formation sensing signal output from the camera discriminating circuit 149 is input into the video processing controlling means 24 described in the first embodiment and provided in the camera controlling unit 127. The video processing controlling means 24 delivers a control signal to the picture image enlarging parts 58 and 59 and the picture image contracting parts 61 and 62 by the pixel formation sensing signal from the camera discriminating circuit 149.

The pixel formation sensing means 23 may be formed as in FIG. 17.

In FIG. 17, a pin 143 is provided to project on the rear end surface of the connector 138 of the first externally fitted TV camera 124a but is not provided at the rear end of the connector 138 of the second externally fitted TV camera 124b. In the camera controlling unit 127 to which the connector 138 is connectable, a switch piece 146 forming a switch 144 is energized to the connector side by a coil spring 147 so as to be pressed by the pin 143 to connect contacts 148 against the energizing force of the coil spring 147 in case the connector 138 is connected to the camera controlling unit 127. The contacts 148 are connected to the camera discriminating circuit 149 so that, when the switch 144 is closed, this camera discriminating circuit 149 will sense the connection of the externally fitted TV camera 124a. In case the second externally fitted TV camera 124b is connected, the switch piece 146 will not be pressed, the switch 144 will remain open and the camera discriminating circuit 149 will sense the connection of the second externally fitted TV camera 124b.

In the camera discriminating circuit 149, the pixel formations of the solid state imaging devices provided in the first externally fitted TV camera 124a and the second externally fitted TV camera 124b are stored in advance so that, depending on which externally fitted TV camera is connected, the pixel formation sensing signal may be output.

In FIG. 17, two kinds of externally fitted TV cameras are sensed with one pin 143. However, a plurality of pins 143 may be provided so that the number of the externally fitted TV cameras which can be sensed, that is, the number of the pixel forming elements which can be sensed may be increased.

The other formations, operations and effects are the same as in the first embodiment.

As explained above, according to the present invention, the characteristics of the pixel formation of the solid state imaging device are made the same with respect to two or more types of solid state imaging devices so that the minimum circuit constants may be switched by using electronic endoscopes of different solid state imaging devices, the circuit scale may be made small and the cost may be made low.

What is claimed is:

1. An electronic endoscope apparatus comprising:
   a first endoscope apparatus having a solid state imaging device wherein an object image obtained from an observing window provided in a tip part of an insertable part inserted to a body cavity is formed and is converted to an electric signal to be output;
   a second endoscope apparatus having a solid state imaging device which is different from the solid state imaging device provided in said first endoscope apparatus in shape or number of pixels but the same in at least one pixel forming element;
   a video processing means to which said first and second endoscope apparatuses can be connected, for processing the electric signal output from said solid state imaging device to be a video signal; and
   a displaying means for receiving the signal processed by said video processing means and for displaying said object image as a picture image.

2. An electronic endoscope apparatus according to claim 1 further comprising a pixel formation sensing means for sensing the solid state imaging device provided in the first or second endoscope apparatus and for outputting a control signal, and a video processing controlling means for receiving the control signal output by said pixel formation sensing means and for controlling said video processing means.

3. An electronic endoscope apparatus comprising:
   a first endoscope apparatus having a solid state imaging device wherein an object image obtained from an observing window provided at a tip of an insertable part inserting into a body cavity is formed and is converted to an electric signal to be output;
   a second endoscope apparatus having a solid state imaging device which is different from the solid state imaging device provided in said first endoscope apparatus in shape or number of pixels but the same in at least one pixel forming element;
   a video processing means, to which said first and second endoscope apparatuses can be connected, for processing the electric signal output from said solid state imaging device to be a video signal;
   a displaying means for receiving the signal processed by said video processing means and for displaying said object image as a picture image;
   a pixel formation sensing means for sensing the solid state imaging device provided in the first or second endoscope apparatus and for outputting a control signal; and
   a video processing controlling means for receiving the control signal output by said pixel formation sensing means and for controlling said video processing means.

4. An electronic endoscope apparatus according to claim 1 or 3 wherein the pixel forming element being the same is such that the shape and area of one effective pixel of each said solid state imaging devices are the same.

5. An electronic endoscope apparatus according to claim 1 or 3 wherein the pixel forming element being the same is such that the length of at least one side in the vertical and horizontal directions of one effective pixel of each said solid state imaging devices is the same.

6. An electronic endoscope apparatus according to claim 1 or 3 wherein the pixel forming element being the same is such that the ratio of the number of pixels in the vertical and horizontal directions of the pixels of each said solid state imaging devices is the same.

7. An electronic endoscope apparatus according to claim 1 or 3 wherein the pixel forming element being the same is such that the length of at least one side in the vertical and horizontal directions of the region including the effective pixels and non-effective region of eachof said solid state imaging devices is the same.

8. An electronic endoscope according to claim 1 or 3 wherein at least one of the first endoscope apparatus and the second endoscope apparatus is provided with said solid state imaging device in the tip part of said insertable part and in a rear of said observing window and the object image is formed on said solid state imaging device.

9. An electronic endoscope apparatus according to claim 1 or 3 wherein at least one of said first endoscope apparatus and said second endoscope apparatus is formed of an optical endoscope in which the object image obtained from said observing window is transmitted to an eyepiece part by an image transmitting optical system, and a television camera provided with said solid state imaging device is removably connected to said eyepiece part.

10. An electronic endoscope apparatus according to claim 2 or 3 wherein said pixel formation sensing means detects a resistance value of a resistance provided in said imaging means and senses the solid state imaging device provided in said imaging means.

11. An electronic endoscope apparatus according to claim 2 or 3 wherein said pixelformation sensing means is formed of a switch switched on and off by a projection provided in said imaging means and senses the solid state imaging device by an on-off signal.

12. An electronic endoscope apparatus according to claim 2 or 3 wherein said video processing controlling means has a timing signal generating means receiving the control signal from said pixel formation sensing means and outputting a timing signal corresponding to pixel formation.

13. An electronic endoscope apparatus according to claim 2 or 3 wherein said video processing controlling means is provided with an interpolating coefficient controlling means receiving the control signal from said pixel forming element sensing means, setting an interpolating coefficient and enlarging rate and outputting said interpolating coefficient and enlarging rate to said signal processing means.

14. An electronic endoscope apparatus according to claim 13 wherein said video processing means is provided with a picture image interpolating means receiving the interpolating coefficient and enlarging rate from said interpolating coefficient controlling means and performing interolation and enlargement.

15. An electronic endoscope apparatus according to claim 2 or 3 wherein said video processing controlling means is provided with a master control means receiving the control signal from said pixel formation sensing means and outputting to said video processing means a control signal controlling enlargement or contraction.

16. An electronic endoscope apparatus according to claim 15 wherein said video processing means is provided with a picture image enlarging part, receiving the control signal from said master control means and enlarging the picture image, and a picture image contracting part contracting the picture image.

17. An electronic endoscope apparatus according to claim 15 wherein said video processing controlling means is further provided with a displayed picture image enlarging and contracting switching means which can select a size of a displayed picture image of said displaying means.

* * * * *